United States Patent [19]

Horie et al.

[11] Patent Number: 4,619,880
[45] Date of Patent: Oct. 28, 1986

[54] ELECTROPHOTOGRAPHIC LIGHT SENSITIVE MATERIAL CONTAINS HYDRAZONE COMPOUND

[75] Inventors: Seiji Horie; Naonori Makino; Hideo Sato, all of Kanagawa, Japan

[73] Assignee: Fuji Photo Film Co., Ltd., Kanagawa, Japan

[21] Appl. No.: 743,323

[22] Filed: Jun. 10, 1985

[30] Foreign Application Priority Data

Jun. 8, 1984 [JP] Japan .................................. 59-118416

[51] Int. Cl.$^4$ .............................................. G03G 5/14
[52] U.S. Cl. ......................................... 430/58; 430/59; 430/76
[58] Field of Search ................................... 430/58, 59

[56] References Cited

U.S. PATENT DOCUMENTS 4,399,207  8/1983  Sakai et al. .............................. 430/58
4,481,271 11/1984  Hashimoto et al. ..................... 430/59

Primary Examiner—John D. Welsh
Attorney, Agent, or Firm—Sughrue, Mion, Zinn Macpeak & Seas

[57] ABSTRACT

The integrated type electrophotographic light-sensitive material is disclosed, the material comprising two layers comprising (1) an electric charge generating layer containing an electric charge generating material and (2) an electric charge transporting layer containing an electric charge transporting material, provided on an electrically conductive base, wherein said electric charge generating layer contains at least one hydrazone compound represented by the following general formulas (I)–(V):

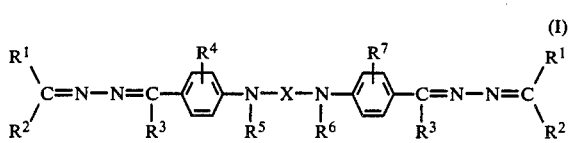

(I)

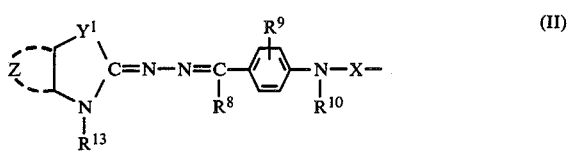

(II)

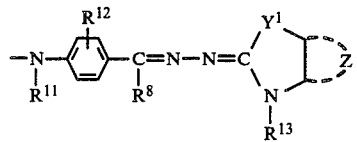

(III)

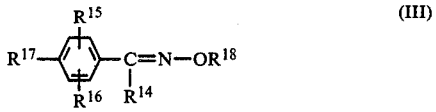

(IV)

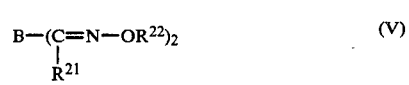

(V)

24 Claims, No Drawings

ELECTROPHOTOGRAPHIC LIGHT SENSITIVE MATERIAL CONTAINS HYDRAZONE COMPOUND

FIELD OF THE INVENTION

The present invention relates to electrophotographic light-sensitive materials comprising an electrophotographic light-sensitive layers containing an electric charge generating substance and an electric charge transporting substance provided on an electrically conductive base.

BACKGROUND OF THE INVENTION

Fundamental characteristics required for electrophotographic light-sensitive materials include (1) the ability to carry out electrification in the dark so as to have a suitable electric potential, (2) the disappearance of electric charges in the dark is small and (3) the electric charges can be rapidly removed by exposing to light.

Hitherto, as photoconductive materials for electrophotographic light-sensitive materials, inorganic substances such as selenium, cadmium sulfide or zinc oxide, etc. have been used.

However, these inorganic substances have various disadvantages. For example, selenium which is currently widely used, satisfies the above-described requirements (1)–(3), but its production requires severe conditions which increase the cost of production, it is difficult to work so as to have a belt-shape because of its poor flexibility, and it is necessary to pay attention to handling because it is sensitive to heat or mechanical impact. Cadmium sulfide and zinc oxide have been used as light-sensitive materials by dispersing in a binder resin. However, they can not be repeatedly used in such a state because they have mechanical poor properties such as smoothness, hardness, tensile strength and friction rsistance, etc.

In recent years, for the purpose of overcoming these disadvantages of inorganic substances, electrophotographic light-sensitive materials using various organic substances have been proposed and some of them have been put into practical use.

However, with organic electrophotographic light-sensitive materials, although the mechanical characteristics and flexibility are improved to some extent, the requirements for electrophotographic light-sensitive materials have not been sufficiently satisfied because they have generally low light sensitivity and are not suitable for repeated use.

The photoconductive process for electrophotographic light-sensitive materials consists of (1) a step of generating electric charges by exposing to light, and (2) a step of transporting electric charges.

As an example of conducting steps (1) and (2) with the same substance, there is a selenium light-sensitive plate. On the other hand, as an example of conducting steps (1) and (2) with different substances, a combination of amorphous selenium and poly-N-vinyl carbazole has been well known. Function separating of electrophotographic light-sensitive materials in which steps (1) and (2) are conducted with different substances have advantages in that the scope of selection of materials to be used for the light-sensitive materials is expanded and, consequently, the electrophotographic characteristics such as sensitivity or receiving electric potential, etc. of the electrophotographic light-sensitive materials are improved. Further, substances advantageous for producing an electrophotographic light-sensitive coating film can be selected from a wide scope.

With respect to such function separating of electrophotographic light-sensitive materials, the proposals to date have not provided satisfactory results.

SUMMARY OF THE INVENTION

An object of the present invention is to provide integrated type light-sensitive materials having high sensitivity, wherein reduction of the charged electric potential is small and the residual electric potential is low even after an endurance test is carried out.

The object of the present invention has been attained by providing integrated type electrophotographic light-sensitive materials comprising two layers comprising an electric charge generating layer containing an electric charge generating material and an electric charge transporting layer containing an electric charge transporting material provided on an electrically conductive base, wherein said electric charge generating layer containes at least one of compounds represented by the following general formulas (I)–(V).

When hydrazone compounds represented by the following general formulas (I)–(V) are selected from many electric charge transporting materials to be used as the electric charge transporting materials to be added to the electric charge generating layer, light-sensitive materials having high sensitivity wherein reduction of the charged electric potential is small when an endurance test is carried out, and the residual electric potential is low, can be obtained.

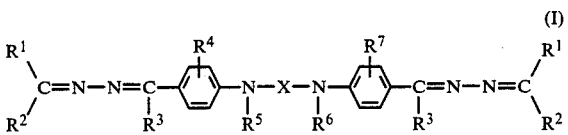

(I)

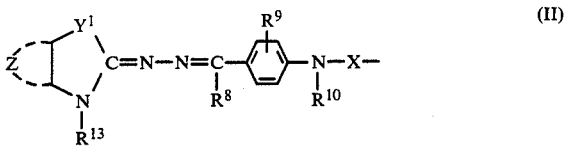

(II)

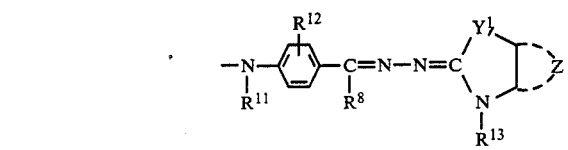

(III)

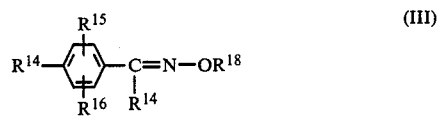

(IV)

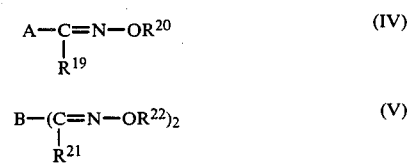

(V)

$R^1$, $R^2$, $R^5$, $R^6$, $R^8$, $R^{10}$, $R^{11}$ and $R^{13}$ each represent an unsubstituted or substituted straight chain or branched chain alkyl group having 1 to 12 carbon atoms, an unsubstituted or substituted straight chain or branched chain aralkyl group having 7 to 20 carbon atoms or an unsubstituted or substituted aryl group having 6 to 20 carbon atoms, or $R^5$ and $R^6$ or $R^{10}$ and $R^{11}$ may form a N-containing heterocyclic group by bonding each other, and $R^5$ and $R^6$, and $R^{10}$ and $R^{11}$ may be identical or different from each other.

$R^3$, $R^8$ $R^{14}$, $R^{18}$, $R^{19}$, $R^{20}$ and, $R^{21}$, and $R^{22}$ each represent a hydrogen atom, an unsubstituted or substituted straight chain or branched chain alkyl group having 1 to 12 carbon atoms, an unsubstituted or substituted aralkyl group having 7 to 20 carbon atoms or an unsubstituted or substituted aryl group, and $R^3$, $R^8$, $R^{14}$, $R^{18}$, $R^{19}$, $R^{20}$, $R^{21}$ and $R^{22}$ and may be identical or different from each other.

$R^4$, $R^7$, $R^9$, $R^{12}$, $R^{15}$ and $R^{16}$ each represent a hydrogen atom, an unsubstituted or substituted straight chain or branched chain alkyl group having 1 to 12 carbon atoms, an unsubstituted or substituted aralkyl group having 7 to 20 carbon atoms, an unsubstituted or substituted aryl group having 6 to 20 carbon atoms, a halogen atom, an alkoxy group having 1 to 20 carbon atoms or an aryloxy group having 6 to 20 carbon atoms.

$R^4$, $R^7$, $R^9$, $R^{12}$, $R^{15}$ and $R^{16}$ may be identical or different from each other.

$R^{17}$ represents an alkoxy group, an aralkyloxy group or a substituted amino group represented by

wherein $R^{23}$ and $R^{24}$ each represent the same substituent as described above, from $R^5$ and $R^6$.

X represents the following general formula:

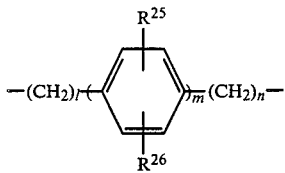

wherein l and n each represents 0 or an integer of 1 to 6, m represents 0 or 1.

$R^{25}$ and $R^{26}$ each represent the same substituent as described above for $R^4$ and $R^7$. $R^{25}$ and $R^{26}$ may form a condensed polynuclear aromatic ring by bonding to each other.

$Y^1$ represents an oxygen atom, a sulfur atom, a selenium atom, a substituted or unsubstituted imino group or an unsubstituted or substituted methylene group.

Z represents an atomic group necessary to form a benzene or naphthalene ring.

A represents a substituted or unsubstituted condensed carboxylic ring or a monocyclic ring, condensed 5 member heterocyclic ring or condensed 6 member heterocyclic ring represented by the following structural formula:

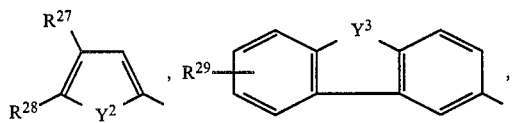

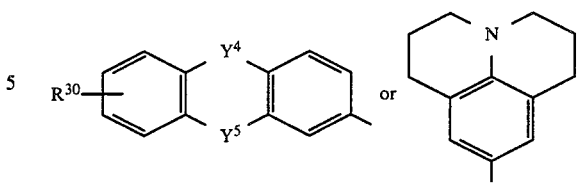

wherein $Y^2$, $Y^3$, $Y^4$ and $Y^5$ each represent S, O or N—$R^{31}$ ($R^{31}$ represents an alkyl group having 1 to 4 carbon atoms), which may be the same kind or different kinds of atom, $R^{27}$ and $R^{28}$ which may be identical or different each represent a hydrogen atom, an alkyl group or an alkoxy group, or $R^{27}$ and $R^{28}$ represent a group capable of forming a benzene ring or a naphthalene ring by linking together, and $R^{29}$ and $R^{30}$ each represents a hydrogen atom, an alkyl group, an alkoxy group, an aryloxy group, an acyl group, an alkoxycarbonyl group, an aryloxycarbonyl group, a halogen atom, a monoalkylamino group, a dialkylamino group, an amido group or a nitro group, which may be substituted or unsubstituted, and B represents a substituted or unsubstituted arylene group.

DETAILED DESCRIPTION OF THE INVENTION

When $R^1$, $R^2$, $R^5$, $R^6$, $R^{10}$, $R^{11}$, $R^{13}$, $R^{23}$ and $R^{24}$ are unsubstituted alkyl groups, examples of them include methyl group, ethyl group, propyl group, butyl group, pentyl group, hexyl group, octyl group, nonyl group, dodecyl group, isopropyl group, isobutyl group, isopentyl group, 4-methylpentyl group, sec-butyl group and tert-butyl group. In case that they are substituted alkyl groups, examples of substituents include chlorine, bromine and fluorine as halogen atoms, methoxy group, ethoxy group, propoxy group, butoxy group and pentyloxy group as alkoxy groups, phenoxy group, o-tolyloxy group, m-tolyloxy group, p-tolyloxy group, 1-naphthyloxy group and 2-naphthyloxy group as aryloxy groups, dimethylamino group, diethylamino group, dipropylamino group, N-methyl-N-ethylamino group, N-ethyl-N-propylamino group and N-methyl-N-propylamino group as dialkylamino group, methylthio group, ethylthio group and propylthio group as alkylthio groups, and piperidino group, 1-piperazinyl group, morpholino group and 1-pyrrolidyl group as N-containing heterocyclic groups.

Examples of the substituted alkyl groups are alkyl groups wherein at least one of the above described substituents are bonded to any of the carbon atoms of the above described alkyl groups.

When $R^1$, $R^2$, $R^5$, $R^6$, $R^{10}$, $R^{11}$, $R^{13}$, $R^{23}$ and $R^{24}$ are unsubstituted aralkyl groups, examples of them include benzyl group, phenetyl group; 1-naphthylmethyl group, 2-naphthylmethyl group, 1-anthrylmethyl group and benzohydryl group. In case that they are substituted aralkyl groups, examples of substituents include the above described substituents.

Examples of the substituted aralkyl groups are aralkyl groups wherein at least one of the above-described substituents are bonded to any of the carbon atoms of the above described aralkyl groups.

When $R^1$, $R^2$, $R^5$, $R^6$, $R^{10}$, $R^{11}$, $R^{13}$, $R^{23}$ and $R^{24}$ are unsubstituted aryl groups, examples of them include phenyl group, 1-naphthyl group, 2-naphthyl group, anthryl group, pyrenyl group, acenaphthenyl group and fluorenyl group. In case that they are substituted aryl groups, examples of substituents include methyl group, ethyl group, propyl group, butyl group, pentyl group, isopropyl group, isobutyl group and isopentyl group as alkyl groups in addition to the above described susbtituents. Examples of the substituted aryl groups are aryl groups wherein at least one of the above described substituents are bonded to any of the carbon atoms of the above described aryl groups.

When $R^3$, $R^4$, $R^7$, $R^8$, $R^9$, $R^{10}$, $R^{12}$, $R^{14}$, $R^{15}$, $R^{16}$, $R^{18}$, $R^{19}$, $R^{20}$, $R^{21}$, $R^{22}$, $R^{25}$ and $R^{26}$ are unsubstituted or substituted alkyl groups, unsubstituted or substituted aralkyl groups, or unsubstituted or substituted aryl groups, examples of them are the same as those in case of $R^1$, $R^2$, $R^5$, $R^6$, $R^{10}$, $R^{11}$, $R^{13}$, $R^{23}$ and $R^{24}$.

When $R^4$, $R^7$, $R^9$, $R^{12}$, $R^{15}$, $R^{16}$, $R^{25}$ and $R^{26}$ are halogen atoms, alkoxy groups or aryloxy groups, examples of them include chlorine, bromine and fluorine as halogen atoms, methoxy group, ethoxy group, propoxy group, butoxy group and pentyloxy group as alkoxy groups, and phenoxy group, o-tolyloxy group, m-tolyloxy group, p-tolyloxy group, 1-naphthyloxy group and 2-naphthyloxy group as aryloxy groups.

When $R^5$ and $R^6$ or $R^{10}$ and $R^{11}$ or $R^{23}$ and $R^{24}$ form a N-containing heterocyclic group by bonding tegether, a preferable example of it is piperazine group and morpholino group.

Examples of suitable substituents are phenyl group, dimethylaminophenyl group and diethylaminophenyl group as $R^1$ and $R^2$, hydrogen atom, methyl group, ethyl group, phenyl group, benzyl group, p-(dimethylamino)phenyl group and P-(diethylamino)phenyl group as $R^3$, $R^8$, $R^{14}$, $R^{19}$ and $R^{21}$, hydrogen atom, methyl group, ethyl group, methoxy group, ethoxy group, bormine atom, chlorine atom and fluorine atom as $R^4$, $R^7$, $R^9$, $R^{12}$, $R^{15}$, $R^{16}$, $R^{25}$, and $R^{26}$, methyl group, ethyl group, n-butyl group, n-hexyl group, benzyl group and phenyl group as $R^5$, $R^6$, $R^{10}$, $R^{11}$, $R^{23}$ and $R^{24}$, and methyl group, ethyl group and benzyl group as $R^{13}$.

Examples of X include methylene group, ethylene group, propylene group, butylene group, pentylene group, hexylene group, laurylene group, p-xylylene group, 2,5-dichloro-p-xylylene group, 2,3,5,6-tetramethyl-p-xylylene group and 1,4-dimethylenenaphthalene group.

Preferable examples of X include ethylene group, butylene group, pentylene group, hexylene group and p-xylylene group.

Examples of $Y^1$ include oxygen atom, sulfur atom, selenium atom, alkylimino group and dimethylmethylene group. The alkyl group in the alkylimino group is that which has 1 to 8 carbon atoms. As $Y^1$, sulfur atom is preferable.

In compounds represented by the general formulas (III)–(V), as alkoxy groups and aralkyloxy groups of $R^{17}$, there are alkoxy groups having 1 to 12 carbon atoms and aralkyloxy groups having 7 to 12 carbon atoms, examples of which include methoxy group, ethoxy group, propoxy group, butoxy group, octyloxy group and benzyloxy group.

As examples of $R^{17}$, substituted amino groups are preferred, and substituted amino groups wherein $R^{23}$ and $R^{24}$ each represent a methyl group, an ethyl group, a benzyl group, a phenyl group or a tolyl group are preferred. Particularly suitable examples are dimethylamino group, diethylamino group, dibenzylamino group, diphenylamino group and N-ethyl-N-phenylamino group.

As examples of $R^{18}$, $R^{20}$ and $R^{22}$, there are hydrogen atom, alkyl groups having 1 to 12 carbon atoms such as methyl group, ethyl group, propyl group, octyl group, etc., aralkyl gropus having 7 to 24 carbon atoms such as benzyl group, phenetyl group, ω-ω-diphenylpropyl group, etc., and substituted or nonsubstituted phenyl groups, etc. Examples of the substituted phenyl groups are the same as those of substituted phenyl groups represented by $R^1$, $R^2$, $R^5$, $R^6$, $R^{10}$, $R^{11}$ and, $R^{13}$, $R^{23}$ and $R^{24}$. A particularly suitable example of $R^{18}$, $R^{20}$ and $R^{22}$ is benzyl group.

Examples of condened carbocyclic groups represented by A include condensed carboxylic group having 10 to 20 carbon atoms such as 1-naphthyl group, 2-naphthyl group, 9-anthracenyl group, 1-pyrenyl group etc.

Examples of $R^{27}$ and $R^{28}$ in the heterocyclic groups represented by A include a hydrogen atom; alkyl groups having 1 to 4 carbon atoms such as methyl group, ethyl group, propyl group, butyl group, etc.; alkoxy groups having 1 to 4 carbon atoms such as methoxy group, ethoxy group, propoxy group, butoxy group, etc., and groups capable of forming a benzene ring or a naphthalene ring by linking $R^{27}$ with $R^{28}$.

Examples of $R^{29}$ and $R^{30}$ include the same alkyl groups as substituted or unsubstituted alkyl groups represented by $R^1$, $R^2$, $R^5$, $R^6$, $R^{10}$, $R^{11}$, $R^{13}$, $R^{23}$ and $R^{24}$ alkoxy groups having 1 to 4 carbon atoms, aryloxy groups having 6 to 10 carbon atoms, acyl groups having 2 to 11 carbon atoms; alkoxycarbonyl groups having 2 to 5 carbon atoms, aryloxycarbonyl groups having 7 to 11 carbon atoms, halogen atoms, monoalkylamino groups 1 to 4 carbon atoms, dialkylamino groups having 1 to 4 carbon atoms, amido groups having 2 to 9 carbon atoms and nitro group. They may be substituted or unsubstituted.

Examples of them include methoxy group, ethoxy group, propoxy group and butoxy group as alkoxy groups having 1 to 4 carbon atoms; phenoxy group and o-, m- or p-tolyoxy groups as aryloxy groups having 6 to 10 carbon atoms; acetyl group, propionyl group, benzoyl group and o-, m- or p-toluoyl group as acyl groups having 2 to 11 carbon atoms; methoxycarbonyl group, ethoxycarbonyl group, propoxycarbonyl group and butoxycarbonyl group as alkoxy-carbonyl groups having 2 to 5 carbon atoms; phenoxycarbonyl and o-, m- or p-tolyloxycarbonyl group as aryloxycarbonyl groups having 7 to 11 carbon atoms; chlorine atom, bromine atom and fluorine atom as halogen atom; methylamino group, ethylamino group, and butylamino group as monoalkylamino groups substituted by an alkyl group having 1 to 4 carbon atoms; dimethylamino group, diethylamino group, dipropylamino group, dibutylamino group and N-methyl-N-ethylamino group as dialkylamino groups substituted by alkyl groups having 1 to 4 carbon atoms; acetamide group and propionamide group as amide groups; and nitro group.

$Y^2$ and $Y^3$ represent each S, O or N—$R^{31}$. $R^{31}$ represents an alkyl group having 1 to 4 carbon atoms such as a methyl group, ethyl group, propyl group or butyl group.

Examples of 5-member heterocyclic ring represented by A include 2-furyl group, 2-thienyl group, 1-methyl-2-pyrrolyl group and 5-methyl-2-thienyl group, examples of condensed 5-member heterocyclic rings include 2-benzo(b)-thienyl group, 2-naphtho(2,3-b)thienyl group, 9-ethylcarbazol-2-yl group and dibenzothiophen-2-yl group, and examples of condensed 6 member heterocyclic rings include 2-phenoxathienyl group, 10-ethylphenoxazin-3-yl group and 10-ethylphenothiazin-3-yl group. Preferred examples include 5-methyl-2-thienyl group, 2-benzo(b)thienyl group, 9-ethylcarbazol-2-yl group, dibenzothiophen-2-yl group and 10-ethylphenothiazin-3-yl group.

Examples of B include phenylene group and naphthalene group. When having substituents, example of the substituents are the same as those of $R^4$, $R^7$, $R^9$, $R^{12}$, $R^{15}$, $R^{16}$, $R^{25}$ and $R^{26}$.

Examples of compounds represented by the general formulas (I)–(V) are described.

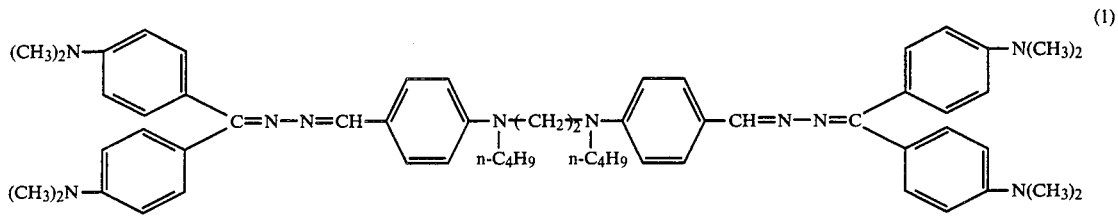

(1)

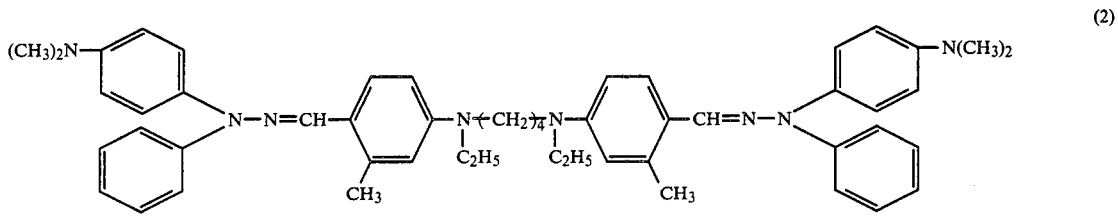

(2)

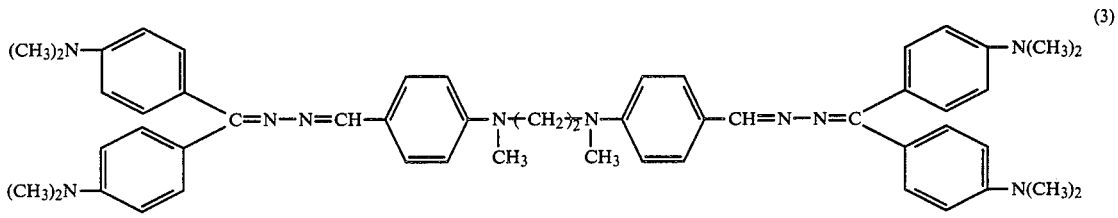

(3)

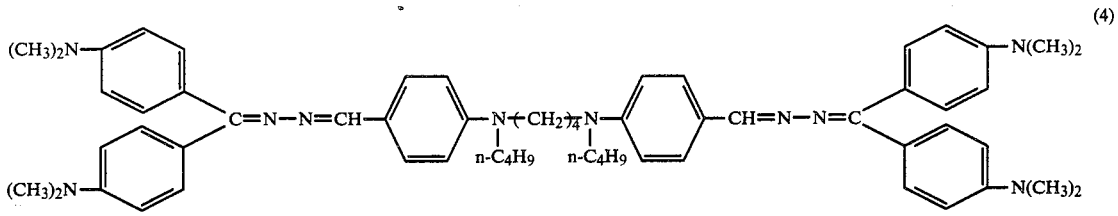

(4)

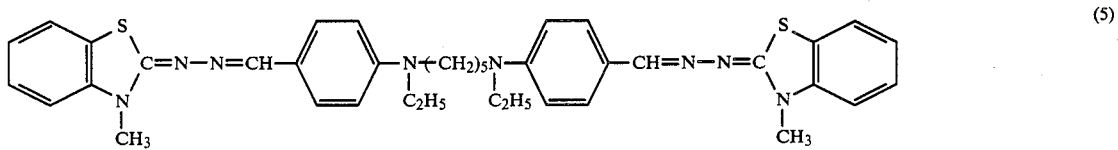

(5)

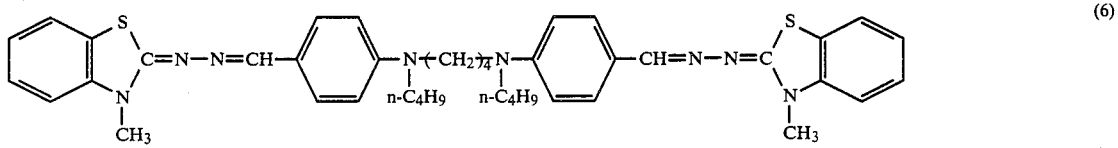

(6)

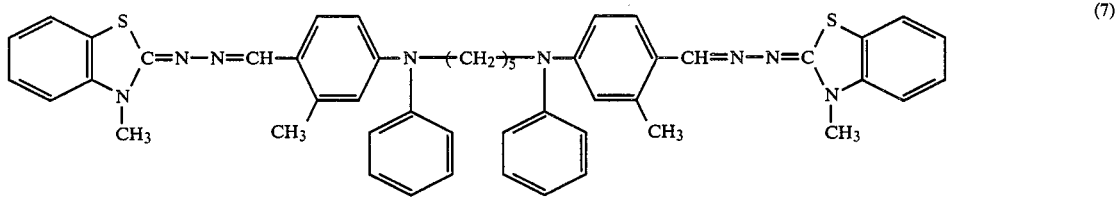

(7)

-continued

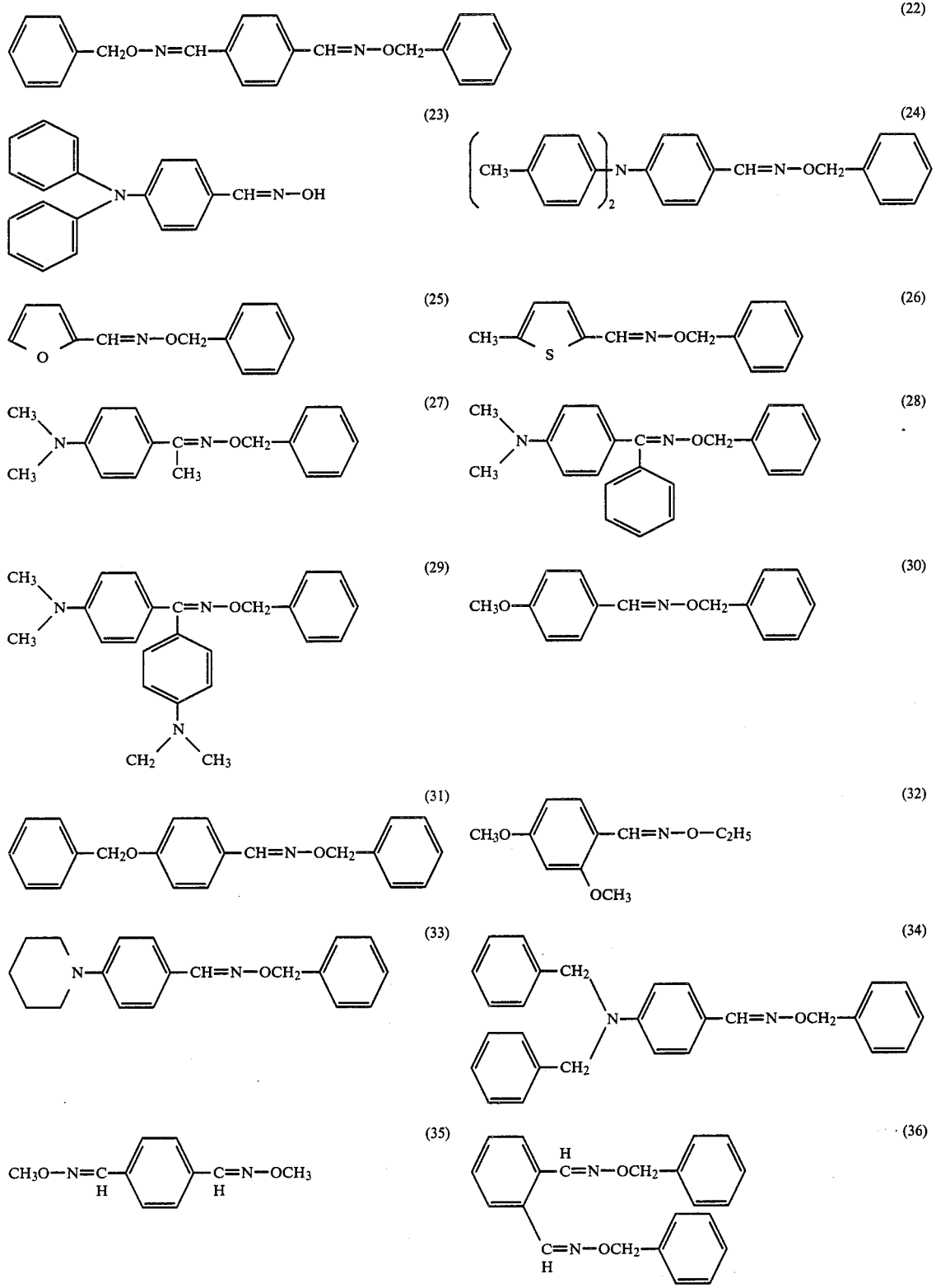

The hydrazone compounds represented by the above described formulae (I) and (II) can be produced by processes described in the technical literature. Examples of such literature include *Preparative Organic Chemistry*, edited by G. Hilgetag and A. Martini (John Wiley & Sons, Ltd., New York, 1968), pages 508 et seq; *The Chemistry of the Carbon-Nitrogen Double Bond*, edited by S. Patai (Interscience Publishers, London, 1970), pages 71 et seq; an synthesis of a group of bisaldehydes is described in P. W. Hickmott, *J. Chem. Soc.*, (c), 1966 p. 666. More specifically, they can be produced by reacting a hydrazine represented by one of formulae (VI) to (VII) below, or a mineral acid salt therof, with bisaldehyde or bisketone represented by formulas (VIII) and (IX) below, in a solvent, adding, if necessary, a small amount of acid (e.g., glacial acetic acid or an inorganic acid) as a condensating agent. As the solvent, alcohols such as methanol, ethanol, etc., tetrahydrofuran, acetic acid, DMF (dimethyl formamide), etc., can be used alone or as a mixture thereof.

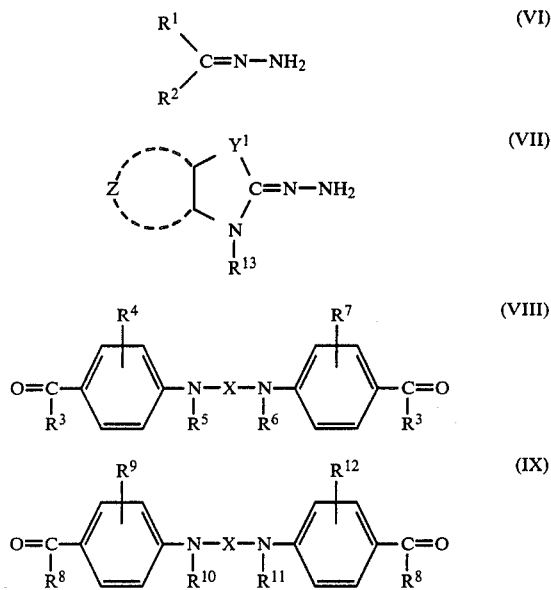

$R^1$ through $R^{10}$, X, $Y^1$, and Z in the formulae (VI) to (IX) each represent the same meanings as in the formulae (I) and (II).

The hydrazone compounds represented by the general formulas (III), (IV) and (V) are synthesized according to the processes described in Japanese Patent Application (OPI) No. 107545/84. (The term "OPI" as used herein refers to a "published unexamined Japanese Patent Application".

In the integrated type electrophotographic light-sensitive materials of the present invention, electric charge generating materials used for the electric charge generating layer can include the following materials.

(1) Selenium and selenium alloys.

(2) Inorganic photoconductive substances such as CdS, CdSe, CdSSe, ZnO, and ZnS.

(3) Phthalocyanine pigments such as metal phthalocyanines or metal-free phthalocyanines.

(4) Azo pigments.

For example, azo pigments having a carbazole skeleton as described in Japanese Patent Application (OPI) No. 95033/78 corresponding to U.S. Pat. No. 4,293,628, azo pigments having a triphenylamine skeleton as described in Japanese Patent Application (OPI) No. 132547/78 corresponding to U.S. Pat. No. 4,279,981, azo pigments having a styrylstilbene skeleton as described in Japanese Patent Application (OPI) No. 133445/78 corresponding to U.S. Pat. No. 4,272,598 and Japanese Patent Application (OPI) No. 42352/84, azo pigments having a naphthalene skeleton as described in Japanese Patent Application (OPI) Nos. 1,23541/83 and 192042/83, trisazo pigments as described in Japanese Patent Application (OPI) No. 217556/83, and azo pigments having a thiophene skeleton as described in Japanese Patent Application No. 19042/83.

(5) Perylene pigments such as perylenic acid anhydride or perylenic acid imide, etc.

(6) Indigoid dyes.

(7) Quinacridone pigments, (8) Polynuclear quinones such as anthraquinones, pyrenequinones, anthanthrones, flavanthrones, etc.

(9) Bisbenzimidazole pigments.

(10) Cyanine dyes.

(11) Squaric methine dyes.

(12) Indanthrone pigments.

(13) Xanthene dyes.

(14) Electric charge transfer complexes composed of an electron donative substance such as poly-N-vinylcarbazole, etc. and an electron-accepting substance such as trinitrofluorenone, etc.

(15) Eutectic crystal complexes formed from a pyrylium salt dye and a polycarbonate resin.

(16) Amorphous silicon.

The electric charge transporting materials used for the electric charge transporting layer are classified into two kinds, namely, electron transporting compounds and hole transporting compounds. In the electrophotographic light-sensitive materials of the present invention, both of them can be used.

As the electron transporting compounds, there are compounds having an electron attractive group, for example, 2,4,7-trinitro-9-fluorenone, 2,4,5,7-tetranitro-9-fluorenone, 9-dicyanomethylene-2,4,7-trinigrofluorenone, 9-dicyanomethylene-2,4,5,7-tetranitrofluorenone, tetranitrocarbazole chloranil, 2,3-dichloro-5,6-dicyanobenzoquinone, 2,4,7-trinitro-9,10-phenanthrenequinone, tetrachlorophthalic acid anhydride, tetracyanoethylene and tetracyanoquinodimethane, etc.

As the hole transporting compounds, there are compounds having an electron donative group. For example, (A) high polymers such as (1) Polyvinyl carbazole and derivatives thereof described in Japanese Patent Publication No. 10966/59, (2) Vinyl polymers such as polyvinyl pyrene, polyvinyl anthracene, poly-2-vinyl-4-(4'-dimethylaminophenyl)-5-phenyloxazole or poly-3-vinyl-N-ethylcarbazole, described in Japanese Patent Publication Nos. 18674/68 (U.S. Pat. No. 3,232,755) and 19192/68 (U.S. Pat. No. 3,162,532), (3) Polymers such as polyacenaphthylene, polyindene or acenaphthylene-styrene copolymer described in Japanese Patent Publication No. 19293/68 (U.S. Pat. No. 3,169,060), (4) Condensation resins such as pyrene-formaldehyde resin, bromopyrene-formaldehyde resin or ethylcarbazole-formaldehyde resin described in Japanese Patent Publication No. 13940/81 (U.S. Pat. Nos. 3,842,038 and 3,881,922), or (5) Various triphenylmethane polymers described in Japanese Patent Application (OPI) Nos. 90883/81 and 161550/81, and low molecular weight compounds such as (6) Triazole derivatives described in U.S. Pat. No. 3,112,197, (7) Oxadiazole derivatives described in U.S. Pat. No. 3,189,447, (8) Imidazole derivatives described in Japanese Patent Publication No. 16096/62, (9) Polyarylalkane derivatives described in U.S. Pat. Nos. 3,615,402, 3,820,989 and 3,542,544, Japanese Patent Publication Nos. 555/70 (U.S. Pat. No. 3,542,547) and 10983/76 (U.S. Pat. No. 3,963,799), and Japanese Patent Application (OPI) Nos. 93224/76 (U.S. Pat. No. 4,127,412), 108667/80, 156953/80 and 36656/81,

(10) Pyrazoline derivatives and pyrazolone derivatives described in U.S. Pat. Nos. 3,180,729 and 4,278,746 and Japanese Patent Application (OPI) Nos. 88064/80, 88065/80, 105537/74 (U.S. Pat. No. 3,837,851), 51086/80, 80051/81, 88141/81, 45545/82, 112637/79 and 74546/80,

(11) Phenylenediamine derivatives described in U.S. Pat. No. 3,615,404, Japanese Patent Publication No. 10105/76. Japanese Patent Application (OPI) Nos. 83435/79, 110836/79 and 119925/79, and Japanese Patent Publication Nos. 3712/71 and 28336/72,

(12) Arylamine derivatives described in U.S. Pat. No. 3,567,450, Japanese Patent Publication No. 35702/74, West German Patent (DAS) No. 1,110,518, U.S. Pat. Nos. 3,180,703, 3,240,597, 3,658,520, 4,232,103, 4,175,961 and 4,012,376, Japanese Patent Application (OPI) Nos. 144250/80 and 119132/81, Japanese Patent Publication No. 27577/64, and Japanese Patent Application (OPI) No. 22437/81,

(13) Amino substituted chalcone derivatives described in U.S. Pat. No. 3,526,501,

(14) N,N-bicarbazyl derivatives described in U.S. Pat. No. 3,542,546,

(15) Oxazole derivatives described in U.S. Pat. No. 3,257,203,

(16) Styrylanthracene derivatives described in Japanese Patent Application (OPI) No. 46234/81,

(17) Fluorenone derivatives described in Japanese Patent Application (OPI) No. 110837/79, or

(18) Hydrazone derivatives described in U.S. Pat. No. 3,717,462, Japanese Patent Application (OPI) Nos. 59143/79 (corresponding to U.S. Pat. No. 4,150,987), 52063/80 (U.S. Pat. No. 4,338,388), 52064/80, 46760/80, 85495/80, 11350/82, 148749/82 and 104144/82.

In the present invention, the electric charge conveying compounds are not restricted to compounds shown in (1)–(36), and any known electric charge conveying compounds can be used. These electric charge conveying materials can be used, if necessary, as a combination of two or more thereof.

In the production of the electrophotographic light-sensitive materials of the present invention, the electric charge generating layer may be formed on the electric charge transporting layer or under the electric charge transporting layer.

However, from the viewpoint of practical use, it is preferred that the electrically conductive base, the electric charge generating layer and the electric charge transporting layer are superimposed in this order in view of the mechanical strength.

Such lamination type electrophotographic light-sensitive materials are produced by a process which comprises applying an electric charge generating material to an electrically conductive base by vacuum evaporation, or appying a solution prepared by dissolving in a solvent such as amine, etc., or applying a dispersion prepared by dispersing fine grains of the electric charge generating material in a suitable solvent, dissolving, if necessary, a binder, and drying, and thereafter applying a solution containing an electric charge transporting material and a binder to the resulting layer and drying.

In this case, the electric charge generating layer is preferred to have a thickness of $4\mu$ or less and, preferably, $2\mu$ or less, and the electric charge transporting layer is preferred to have a thickness of 3 to $30\mu$ and, preferably 5 to $20\mu$.

When forming the electric charge generating layer of coating, the amount of electric charge generating material used is 0.1 times by weight or more, preferably 0.01 to 5 times by weight, more preferably 0.05 to 2 times by weight based on the binder resin. If the amount is less than the above described value, a sufficient sensitivity is not obtained. The amount of the electric charge transporting material in the electric charge transporting layer is preferred to be 0.1 to 2 times by weight and, preferably, 0.3 to 1.3 times by weight based on the binder.

The above described electric charge generating layer contains at least one compounds represented by the above described general formulas (I)–(V) as an essential component. The amount of such is 10 times by weight or less and, preferably, 0.01 to 2 times by weight of the electric charge generating material.

As the electrically conductive bases used for the electrophotographic light-sensitive materials of the present invention, there are metal plates such as those of aluminium, copper, zinc, etc., plastic sheets or plastic films such as those of polyester, etc., to which an electrically conductive material such as $SnO_2$ is applied by vacuum evaporation or by coating of a dispersion, and paper which is subjected to processing so as to have an electrically conductive property.

As the binders, electrically insulating film-forming high polymers which are hydrophobic and have a high dielectric constant are preferred. Examples of such high polymers include the following materials. Of course, the high polymers are not restricted to them.

Polycarbonate, polyester, methacryl resin, acryl resin, polyvinyl chloride, polyvinylidene chloride, polystyrene, polyvinyl acetate, styrene-butadiene copolymer, vinylidene chloride-acrylonitrile copolymer, vinyl chloride-vinyl acetate copolymer, vinyl chloride-vinyl acetatemaleic acid anhydride coplymer, silicaone resin, siliconealkyd resin, phenol-formaldehyde resin, styrenealkyd resin and poly-N-vinylcarbazole. These binders can be used alone or as a mixture of two or more of them. The binders are incorporated in an amount of from 10 to 90 wt% based on the solid in the charge generating layer, and in an amount of from 0 to 95 wt%, preferably 20 to 90 wt% based on the solid in the charge transporting layer.

When producing the electrophotographic light-sensitive materials of the present invention, additives such as plasticizers, sensitizers, etc. may be used together with binders.

As the plasticizers, there are biphenyl, chlorinated biphenyl, o-terphenyl, p-terphenyl, dibutyl phthalate, dimethyl glycol phthalate, dioctyl phthalate, triphenyl phosphate, methylnaphthalene, benzophenone, chlorinated paraffin, polypropylene, polystyrene, dilaurylthio-dipropionate, 3,5-dinitrosalicylic acid and various fluorohydrocarbons, etc.

In addition, in order to improve the surface properties of the electrophotographic light-sensitive materials, silicone oil, etc. may be added.

As the sensitizing agents, there are chloranil, tetracyanoethylene, Methyl Violet, Rhodamine B, cyanine dyes, merocyanine dyes, pyrylium dyes, thiapyrylium dyes, etc.

If necessary, an adhesive layer or a barrier layer may be provided between the electrically conductive base and the light-sensitive layer. As materials used for these layers, there are gelatine, casein, polyvinyl alcohol, ethyl cellulose, carboxymethyl cellulose, vinylidene chloride polymer latex described in Japanese Patent Application (OPI) No. 84247/84, styrene-butadiene polymer latex described in Japanese Patent Application (OPI) No. 115544/84 and aluminium oxide as well as the above described high polymers used as the binder. These layers are preferred to have a thickness of 1μ or less.

The electrophotographic light-sensitive materials of the present invention generally have characteristics of having high sensitivity and excellent durability.

The electrophotographic light-sensitive materials of the present invention can be used not only for electrophotographic copying machines but also widely used in the field of light-sensitive materials for printers using laser of a Braun tube as a light source.

In the following, the present invention is illustrated in greater detail with reference to examples, but the present invention is not restricted to the examples. In the examples, "part" means "part by weight".

EXAMPLE 1

To a solution obtained by dissolving 3 parts of a compound represented as exemplified compound (6) and 5 parts of polyester resin (trade name: Vylon 200, produced by Toyo Spinning Co.) in 44 parts of tetrahydrofuran, 5 parts of a disazo pigment having the following structure were added. After the mixture was processed for 20 hours by a ball mill, the dispersion was applied to an electrically conductive base (a 75μ polyethylene terephthalate film having an aluminium film applied to the surface thereof by vacuum evaporation; surface electric resistance: $10^3$ Ω) by a wire wound rod and dried to produce an electric charge generating layer having a thickness of 0.6 μm. (Disazo pigment)

Disazo pigment

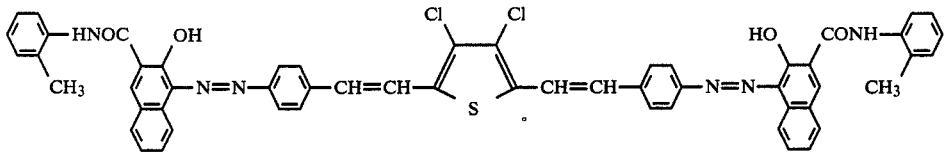

To the electric charge generating layer, a solution prepared by dissolving 2.4 parts of the hydrazone compound having the following structure which was an electric charge transporting substance and 4 parts of a polycarbonate of bisphenol A in a mixture of 13.3 parts of dichloromethane and 26.6 parts of 1,2-dichloroethane was applied with a wire would rod and dried to form an electric charge transporting layer having a thickness of 11μ. Thus, sample 1, an electrophotographic light-sensitive material having an electrophotographic light-sensitive layer consisting of two layers was produced.

(Hydrazone compound)

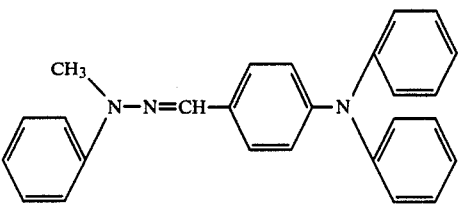

On the other hand, for comparison, Comparative Sample 1 in which compound (6) was not added to the electric charge generating layer was produced in the same manner as Sample 1.

These electrophotographic light-sensitive materials were electrified by corona discharge at +5 KV by means of a testing apparatus for electrostatic copying paper (Type SP-428, produced by Kawaguchi Denki Co.) so as to have −800 V, then they were exposed to light with a tungsten lamp having a color temperature of 2854° K. so as to be 2 luxes on the surface. The time required for reducing the surface electric potential to half of the initial surface electric potential was measured and the half-decay exposure amount ($E_{50}$: Lux.sec) was determined.

The results were as follows:

Sample 1 $E_{50}$: 1.5 Luxes.sec.

Comparative Sample 1 $E_{50}$: 2.0 Luxes.sec.

Further, the steps of electrification and exposure were repeated 200 times, and the first initial electric potential (V) and the charged electric potential (V) after the steps were repeated 200 times were measured.

| | Initial electric potential (V) | Electric potential after repeating 200 times (V) |
|---|---|---|
| Sample 1 | −732 | −718 |
| Comparative Sample 1 | −511 | −150 |

It is understood from the above described results that Sample 1 wherein, the hydrazone compound of the present invention is added to the electric charge generating layer is excellent in sensitivity as compared with Comparative Sample 1, and the lowering of the charged electric potential after repeated use is remarkably improved as compared with the case of Comparative Sample 1.

EXAMPLES 2-11

Samples 2, 3, 4, 5, 6, 7, 8, 9, 10 and 11 were produced by the same manner as in Example 1, except that Compounds 1, 3, 9, 12, 16, 19, 21, 24, 28 and 29 were used, respectively, instead of the Compound (6) and added to the electric charge generating layer of Example 1. They were electrified by corona discharge at −6 KV, and $E_{50}$ was measured.

The variation of charged electric potential after the steps of electrification and exposure were repeated 200 times was measured. The results are shown below.

| Example | Sample No. | E$_{50}$ (Lux·sec) | Charged electric potential | |
|---|---|---|---|---|
| | | | Initial electric potential (V) | Electric potential after repeating 200 times |
| 2 | 2 | 1.5 | −743 | −667 |
| 3 | 3 | 1.7 | −735 | −704 |
| 4 | 4 | 1.9 | −784 | −765 |
| 5 | 5 | 1.6 | −836 | −818 |
| 6 | 6 | 1.8 | −850 | −809 |
| 7 | 7 | 1.5 | −905 | −893 |
| 8 | 8 | 1.6 | −896 | −860 |
| 9 | 9 | 1.6 | −911 | −901 |
| 10 | 10 | 1.5 | −902 | −882 |
| 11 | 11 | 1.4 | −864 | −804 |

It is understood from the results of Examples 1-11 that Samples 1-11 wherein, the hydrazone compound is added to the electric charge generating layer, are excellent in sensitivity as compared with Comparative Sample 1, and the lowering of the charged electric potential after repeated use is remarkably improved as compared with the comparative sample.

EXAMPLE 12

Sample 12 was produced by the same manner as in Example 1, except that a disazo pigment having the following structure was used instead of the disazo pigment in Example 1.

(Disazo pigment)

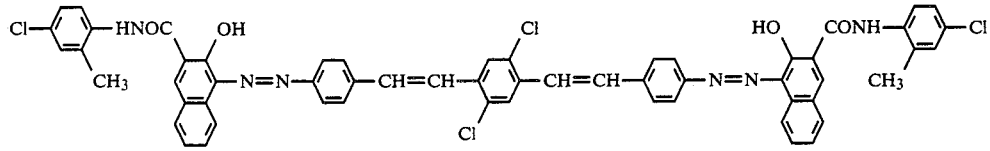

On the other hand, for comparison, Comparative Sample 2 wherein, Compound (6) was not added to the electric charge generating layer, and Comparative Sample 3, wherein the hydrazone compound used as an electric charge transporting material in the electric charge transporting layer of Example 1 was added to the electric charge generating layer were produced.

E$_{50}$ and the variation of the charged electric potential after repeating 5000 times were measured by the same manner as in Example 1. The results are shown below.

| Sample | E$_{50}$ (Lux·sec) | Charged electric potential | |
|---|---|---|---|
| | | Initial electric potential (V) | Electric potential after repeating 5000 times (V) |
| 11 | 2.0 | 796 | 781 |
| Comparative Sample 2 | 2.5 | 782 | 566 |
| Comparative Sample 3 | 2.6 | 751 | 669 |

EXAMPLES 13-16

Samples 13, 14, 15 and 16 were produced by the same manner as in Example 12, except that Compounds (1), (5), (21) and (29) were used, respectively, instead of the Compound (6) to be added to the electric charge generating layer in Example 12.

E$_{50}$ and the variation of the charged electric potential after repeating 5000 times were measured by the same manner as in Example 12. The results are shown below.

| Example | Sample | E$_{50}$ (Lux·sec) | Charged electric potential | |
|---|---|---|---|---|
| | | | Initial electric potential (V) | Electric potential after repeating 5000 times (V) |
| 13 | 13 | 1.9 | 809 | 783 |
| 14 | 14 | 2.1 | 796 | 772 |
| 15 | 15 | 2.0 | 784 | 758 |
| 16 | 16 | 2.0 | 832 | 811 |

It is understood from results in Examples 12-16 that samples wherein the compound represented by the general formula (I)-(V) is added to the electric charge generating layer have very high sensitivity as compared with Comparative Sample 2 wherein no compound is added or Comparative Sample 3 wherein the hydrazone compound used in Example 1 is added, and variation of the charged electric potential thereof after the endurance test is very small.

While the invention has been described in detail and with reference to specific embodiment thereof, it will be apparent to one skilled in the art that various changes and modifications can be made therein without departing from the spirit and scope thereof.

What is claimed is:

1. An integrated type electrophotographic light-sensitive material comprising two layers comprising (1) an electric charge generating layer containing an electric charge generating material and (2) an electric charge transporting layer containing an electric charge transporting material, provided on an electrically conductive base, wherein said electric charge generating layer contains at least one compound represented by the following general formulas (I)-(V):

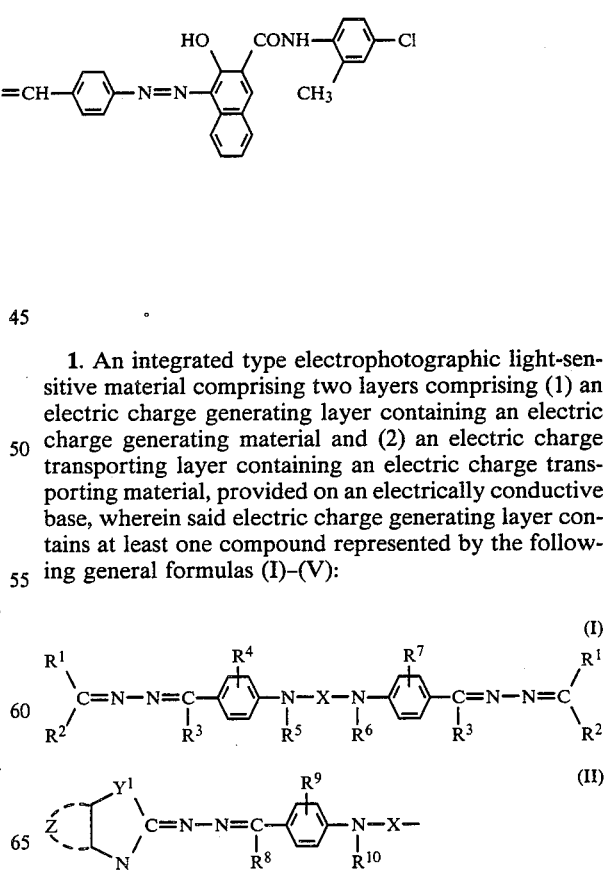

-continued

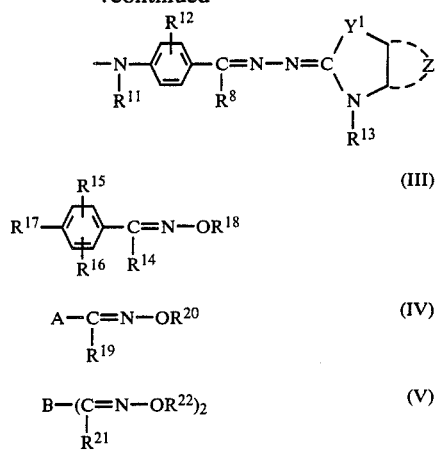

wherein $R^1$, $R^2$, $R^5$, $R^6$, $R^{10}$, $R^{11}$, and $R^{13}$ each represent an unsubstituted or substituted straight chain or branched chain alkyl group having 1 to 12 carbon atoms, an unsubstituted or substituted straight chain or branched chain aralkyl group having 7 to 20 carbon atoms, or an unsubstituted or substituted aryl group, or $R^5$ and $R^6$ or $R^{10}$ and $R^{11}$ may form a N containing heterocyclic group by bonding each other, and $R^5$ and $R^6$, and $R^{10}$ and $R^{11}$ may be identical or different from each other, $R^3$, $R^8$, $R^{14}$, $R^{18}$, $R^{19}$, $R^{20}$, $R^{21}$ and $R^{22}$ and represent a hydrogen atom, an unsubstituted or substituted straight chain or branched chain alkyl group having 1 to 12 carbon atoms, an unsubstituted or substituted aralkyl group having 7 to 20 carbon atoms or an unsubstituted or substituted aryl group, and $R^3$, $R^8$, $R^{14}$, $R^{18}$, $R^{19}$, $R^{20}$, $R^{21}$ and $R^{22}$ may be identical or different from each other, $R^4$, $R^7$, $R^9$, $R^{12}$, $R^{15}$ and $R^{16}$ each represent a hydrogen atom, and unsubstituted or substituted straight chain or branched chain alkyl group having 1 to 12 carbon atoms, an unsubstituted or substituted aralkyl group having 7 to 20 carbon atoms, an unsubstituted or substituted aryl group having 6 to 20 carbon atoms, a halogen atom, an alkoxy group having 1 to 20 carbon atoms or an aryloxy group having 6 to 20 carbon atoms, and $R^4$, $R^7$, $R^9$, $R^{12}$, $R^{15}$ and $R^{16}$ may be identical or different from each other, $R^{17}$ represents an alkoxy group, an aralkyloxy group or a substituted amino group represented by

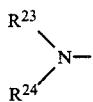

wherein $R^{23}$ and $R^{24}$ each represent the same substituent as described above for $R^5$ and $R^6$ X represents the following general formula:

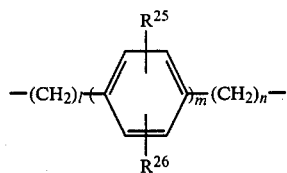

wherein l and n each represnt 0 or an integer of 1 to 6, m represents 0 or 1, and $R^{25}$ and $R^{26}$ represent each the same substituent as described above for $R^4$ and $R^7$, or $R^{25}$ and $R^{26}$ may form a condensed polynuclear aromatic ring by bonding to each other, $Y^1$ represents an oxygen atom, a sulfur atom, a selenium atom, an unsubstituted or substituted imino group or an unsubstituted or substituted methylene group, Z represents an atomic group necessary to form a benzene or naphthalene ring, A represents a substituted or unsubstituted condensed carbocycle or a monocyclic ring or condensed 5 member heterocyclic ring or condensed 6 member heterocyclic ring represented by the following structural formula:

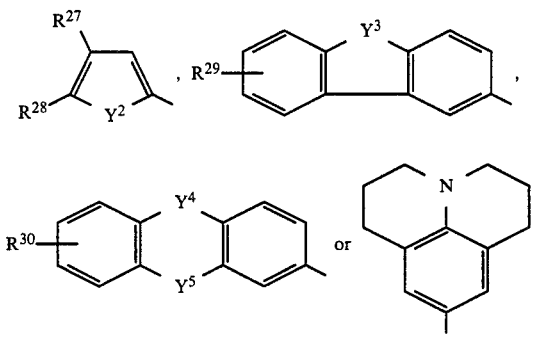

wherein $Y^2$, $Y^3$, $Y^4$ and $Y^5$ each represent S, O or N—$R^{31}$ ($R^{31}$ represents an alkyl group having 1 to 4 carbon atoms), which may be the same kind or different kinds of atom, $R^{27}$ and $R^{28}$ which may be identical or different each represent a hydrogen atom, an alkyl group or an alkoxy group, or $R^{27}$ and $R^{28}$ represent a group capable of forming a benzene ring or a naphthalene ring by linking together, and $R^{29}$, and $R^{30}$ each represents a hydrogen atom, an alkyl group, an alkoxy group, an aryloxy group, and acyl group, an alkoxycarbonyl group, an aryloxycarbonyl group, a halogen atom, a monoalkylamino group, a dialkylamino group, an amido group or a nitro group, which may be substituted or unsubstituted, and B represents a substituted or unsubstituted arylene group.

2. The integrated type electrophotographic light-sensitive material as claimed in claim 1, wherein $R_1$, $R_2$, $R_5$, $R_6$, $R_{10}$, $R_{11}$, $R_{13}$, $R_{23}$ and $R_{24}$ represent an alkyl group selected from the group consisting of methyl group, ethyl group, propyl group, butyl group, pentyl group, hexyl group, octyl group, nonyl group, dodecyl group, isopropyl group, isobuytl group, isopentyl group, 4-methylpentyl group, sec-butyl group and tert-butyl group.

3. The integrated type electrophotographic light-sensitive material as claimed in claim 1, wherein $R_1$, $R_2$, $R_5$, $R_6$, $R_{10}$, $R_{11}$, $R_{13}$, $R_{23}$ and $R_{24}$ represent an aralkyl group selected from the group consisting of benzyl group, phenethyl group, 1-naphthlmethyl group, 2-naphthylmethyl group, 1-anthrylmethyl group and benzohydryl group.

4. The integrated type electrophotographic light-sensitive material as claimed in claim 1, wherein $R_1$, $R_2$, $R_5$, $R_6$, $R_{10}$, $R_{11}$, $R_{13}$, $R_{23}$ and $R_{24}$ represent an aryl group selected from the group consisting of phenyl group, 1-naphthyl group, 2-naphthyl group, anthryl group, pyrenyl group, acenaphthenyl group and fluorenyl group.

5. The integrated type electrophotographic light-sensitive material as claimed in claim 1, wherein $R^5$ and $R^6$ or $R^{10}$ and $R^{11}$ or $R^{23}$ and $R^{24}$ form a piperazine group or morpholino group.

6. The integrated type electrophotographic light-sensitive material as claimed in claim 1, wherein X is selected from the group consisting of methylene group, ethylene group, propylene group, butylene group, pentylene group, hexylene group, laurylene group, p-xylylene group, 2,5-dichloro-p-xylylene group, 2,3,5,6-tetramethyl-p-xylylene group and 1,4-dimethylenenaphthalene group.

7. The integrated type electrophotographic light-sensitive material as claimed in claim 1, wherein $Y^1$ is selected from the group consisting of oxygen atom, sulfur atom, selenium atom, alkylimino group and dimethylmethylene group.

8. The integrated type electrophotographic light-sensitive material as claimed in claim 1, wherein $R^{17}$ is selected from the group consisting of an alkoxy group having 1 to 12 carbon atoms and an aralkyloxy group having 7 to 12 carbon atoms.

9. The integrated type electrophotographic light-sensitive material as claimed in claim 1, wherein $R^{18}$, $R^{20}$ and $R^{22}$ are selected from the group consisting of an hydrogen atom, alkyl groups having 1 to 12 carbon atoms, aralkyl groups having 7 to 24 carbon atoms and substituted or unsubstituted phenyl groups.

10. The integrated type electrophotographic light-sensitive material as claimed in claim 1, wherein $R^{27}$ and $R^{28}$ are selected from the group consisting of a hydrogen atom, alkyl groups having 1 to 4 carbon atoms, alkoxy groups having 1 to 4 carbon atoms and groups capable of forming a benzene ring or a naphthalene ring by linking $R^{27}$ and $R^{28}$.

11. The integrated type electrophotographic light-sensitive material as claimed in claim 1, wherein $Y^2$ and $Y^3$ each represent S, O or N—$R^{31}$ wherein $R^{31}$ represents an alkyl group having 1 to 4 carbon atoms.

12. The integrated type electrophotographic light-sensitive material as claimed in claim 1, wherein A is selected from the group consisting of 2-furyl group, 2-thienyl group, 1-methyl-2-pyrrolyl group and 5-methyl-2-thienyl group.

13. The integrated type electrophotographic light-sensitive material as claimed in claim 1, wherein B is selected from the group consisting of phenylene group and naphthylene group.

14. The integrated type electrophotographic light-sensitive material as claimed in claim 1, wherein the electric charge generating layer is formed on the electrically conductive base and the electric charge transporting layer is formed on the electric charge generating layer.

15. The integrated type electrophotographic light-sensitive material as claimed in claim 1, wherein said electric charge generating layer is formed by coating and the amount of the electric charge generating compound is 0.1 times by weight or more based on the binder resin, and the amount of electric charge transporting compound in the electric charge transporting layers is 0.1 to 2 times by weight based on the binder.

16. The integrated type electrophotographic light-sensitive material as claimed in claim 15, wherein the amount of the electric charge transporting compound in the electric charge transporting layer is 0.3 to 1.3 times by weight based on the binder.

17. The integrated type electrophotographic light-sensitive material as claimed in claim 1, wherein the amount of compound represented by general formula (I)-(V) is 10 times by weight or less of the electric charge generating material.

18. The integrated type electrophotographic light-sensitive material as claimed in claim 17, wherein the amount of compound represented by general formula (I)-(V) is 0.1 to 2 times by weight of the electric charge generating material.

19. The integrated type electrophotographic light-sensitive material as claimed in claim 1, wherein the electric charge generating layer further comprises selenium and selenium alloys, inorganic photoconductive substances, phthalocyanine pigments, azo pigments, perylene pigments, indigoid dyes, quinacridone pigments, polynuclear quinones, bisbenzimidazole pigments, canine dyes, methine dyes, indanthrone pigments, xanthene dyes, electric charge transfer complexes, eutectic crystal complexes, amorphous silicon and mixtures of two or more thereof.

20. The integrated type electrophotographic light-sensitive material as claimed in claim 1, wherein the electric charge transporting layer further comprises an electron transporting compound and/or a hole transporting compound.

21. The integrated type electrophotographic light-sensitive material as claimed in claim 1, wherein the electric charge generating layer has a thickness of $4\mu$ or less.

22. The integrated type electrophotographic light-sensitive material as claimed in claim 21, wherein the electric charge generating layer has a thickness of $2\mu$ or less.

23. The integrated type electrophotographic light-sensitive material as claimed in claim 1, wherein the electric charge transporting layer has a thickness of 3 to $30\mu$.

24. The integrated type electrophotographic light-sensitive material as claimed in claim 23, wherein the electric charge transporting layer has a thickness of 5 to $20\mu$.

* * * * *